(12) United States Patent
Wieland et al.

(10) Patent No.: US 6,991,913 B1
(45) Date of Patent: Jan. 31, 2006

(54) PROCEDURE FOR THE DETERMINATION OF TRIGLYCERIDE CONTAINED IN LOW DENSITY LIPOPROTEIN

(75) Inventors: Heinrich Wieland, St. Peter (DE); Matthias Nauck, Freiburg i. Br. (DE)

(73) Assignee: Roche Diagnostics GmbH, (DE)

( * ) Notice: Subject to any disclaimer, the term of this patent is extended or adjusted under 35 U.S.C. 154(b) by 1104 days.

(21) Appl. No.: 09/597,592

(22) Filed: Jun. 16, 2000

Related U.S. Application Data

(63) Continuation of application No. PCT/EP98/08253, filed on Dec. 16, 1998.

(30) Foreign Application Priority Data

Dec. 17, 1997 (DE) .............................. 197 56 255

(51) Int. Cl.
*C12Q 1/34* (2006.01)

(52) U.S. Cl. ....................................... 435/18

(58) Field of Classification Search ............... 435/6, 435/18

See application file for complete search history.

(56) References Cited

U.S. PATENT DOCUMENTS 4,999,289 A 3/1991 Akiba et al. .................. 435/19

FOREIGN PATENT DOCUMENTS

| DE | 19520210 | | 12/1996 |
|----|----------|---|---------|
| DE | 19520210 A | * | 12/1996 |
| JP | 4326046 A | * | 11/1992 |

OTHER PUBLICATIONS

Pandya et al. The effect of temperature on aggregation behaviour of Pluronics in aqueous solution. Tenside, Surfactants, Detergents, 1994, 31(3), pp. 182-188.*

Nauck, M., et al., "Die LDL- und VLDL - Cholesteringestimmung mit Prazipitationsverfahren. Ein Methodenvergleich mit der Ultrazentrifugationstechnik", *Klin. Lab.*, 40, pp. 167-176 (1994).

Manca, L., et al., "Hb G-Philadelphia, or [α68 ( E17) Asn---> Lys], in North Sardinia: detection by isoelectric focusing and identification by HPLC of tryptic peptides", *Clinica Chimica Acta*, pp. 231-238, (1988).

Schmolka, I.R., "A Review of Block Polymer Surfactants", *The Journal of the American Oil Chemists' Society, 54 (3)*, pp. 110-116, (Mar. 1977).

Siekmeier, R., et al., "Insufficient Accuracy and Specificity of Polyanion Precipitation Methods for Quantifying Low-Density Lipoproteins", *Clinical Chemistry, 36 (12)*, pp. 2109-2113, (1990).

Sugiuchi, H., et al., "Homogeneous assay for measuring low-density lipoprotein cholesterol in serum with triblock copolymer and α-cyclodextrin sulfate", *Clinical Chemistry, 44 (3)*, pp. 522-531, (1998).

* cited by examiner

*Primary Examiner*—David H. Kruse
*Assistant Examiner*—June Hwu
(74) *Attorney, Agent, or Firm*—McDonnell Boehnen Hulbert & Berghoff LLP

(57) ABSTRACT

A procedure is described for the determination of triglyceride contained in low density lipoprotein with the measures that triglyceride-containing lipoprotein is reacted with a non-ionic surface-active agent which is synthesized from a block copolymer of propylene oxide and ethylene oxide, and that a triglyceride determination method is carried out. The procedure is particularly suitable for the in-vitro diagnosis of vascular disorders, in particular in the detection of coronary heart disease.

17 Claims, No Drawings

PROCEDURE FOR THE DETERMINATION OF TRIGLYCERIDE CONTAINED IN LOW DENSITY LIPOPROTEIN

CROSS-REFERENCE TO RELATED APPLICATIONS

This application is a continuation of International Patent Application No. PCT/EP98/08253, filed on Dec. 16, 1998, which claims priority to German Patent Application No. 19756255.8 filed on Dec. 17, 1997.

The present invention relates to a procedure or a diagnostic product for the determination of triglyceride contained in lipoprotein.

Coronary heart disease (CHD) is still the main cause of death in the Western industrial nations. While the importance of cholesterol as a risk factor for coronary heart disease is generally recognized, the assessment of protein-associated triglycerides, in particular of the lipoproteins present in the blood serum, is also taken into consideration in this connection.

As a rule, the division of lipoprotein fractions is carried out, on the basis of differing density, into lipoproteins with very low density ("very low density lipoproteins", abbreviated VLDL below), lipoproteins with low density ("low density lipoproteins", LDL) and lipoproteins with high density ("high density lipoproteins", HDL).

A further specified lipoprotein class is that of the chylomicron (CM).

The lipoproteins can moreover be divided into further subfractions. Among these, particularly the "intermediate density proteins" (IDL) and the "small dense LDL" have great importance for the formation of CHD. The two subfractions of LDL mentioned are particularly triglyceride-rich, so that the LDL triglycerides are more meaningful than the established LDL cholesterol with reference to the CHD risk.

For the diagnosis of vascular diseases, such as coronary heart disease, peripheral arterial occlusive disease and micro- or macroangiopathic changes, the triglyceride content in the individual lipoprotein fractions and the relative amounts contained in the lipoprotein fractions are mutually of importance. For the LDL fraction in particular, it is assumed that a high triglyceride content is associated with coronary heart disease.

Conventional procedures for the determination of triglyceride contained in lipoprotein are essentially based on a two-stage process.

A fractionation step is first carried out in order to separate—as specifically as possible—the respective lipoprotein fractions. A step for the determination of triglyceride in the accordingly separated lipoprotein fractions is then carried out. Different methods are available for the fractionation step.

The precipitation method is primarily designed for the determination of the triglyceride content in lipoproteins of high density (HDL). The selective precipitation of LDL triglycerides has admittedly been attempted. However, the pure precipitation method proved unsuitable, as considerable amounts of VLDL coprecipitate with the LDL fraction, so that a differentiation of the triglyceride content in the respective lipoproteins is only possible with difficulty (see R. Siekmeier et al. in Clin. Chim. Acta 177, p. 231 (1988), R. Siekmeier et al. in Clin. Chem. 36, p. 2109–2113 (1990), and M. Nauck et al. in Klin. Lab. 40, p. 167–176 (1994)).

LDL triglycerides were therefore determined in practice by means of sequential ultracentrifugation, according to their density, in the ultracentrifuge, the period up to the obtainment of the LDL fraction amounting to 48 hours, or by a shortened, combined procedure of ultracentrifugation and precipitation.

In the last-mentioned, relatively selective separation, the VLDL fraction is first separated using the ultracentrifuge (time approximately 24 h), and the remaining LDL fraction is then precipitated more or less selectively by suitable agents (Manual of Laboratory Operation, DHEW No. (NIH) 75-628 National Heart and Lung Institute; Lipid Research Clinics Program, Bethesda, Md., USA, p. 1–74 (1979)).

After this, the amount of LDL triglycerides is determined arithmetically from the triglyceride concentration before and after the LDL precipitation.

Electrophoretic separation of the lipoproteins in a suitable carrier matrix, for example an agarose gel, as described in DE 195 20 210 A1, offers a further fractionation method.

General disadvantages of these conventional procedures for the specific determination of triglycerides in lipoprotein fractions result from the fact that the fractionation steps are both labour- and time-intensive. These conventional methods can also be automated poorly or not at all. Without such a fractionation step, however, the diagnostic result based on lipoprotein-associated triglycerides as a risk factor for vascular diseases is virtually unavailable, as only the selective assignment of the triglyceride content to individual or different lipoprotein fractions allows a meaningful risk assessment. In particular if the LDL triglyceride concentration is regarded as particularly meaningful for the prevention of coronary heart diseases, then the routine detection or determination of the LDL triglycerides is especially desirable.

The invention is therefore based on the object of making available a simple, rapid and reliable procedure for the determination of triglyceride contained in lipoprotein, where a selectivity which is as good as possible with respect to the individual lipoprotein fractions, in particular with respect to the diagnostically particularly meaningful LDL triglyceride content, is made possible.

This object is achieved by a procedure for the determination of triglyceride contained in lipoprotein having the following measures:

a) reaction of triglyceride-containing lipoprotein with a non-ionic surface-active agent, which is synthesized from a block copolymer of propylene oxide and ethylene oxide, and b) carrying-out of a triglyceride determination method.

Further subjects of the present invention consist in a diagnostic product, which is particularly suitable for carrying out this abovementioned procedure, having a) a non-ionic surface-active agent which is synthesized from a block copolymer of propylene oxide and ethylene oxide, and b) agents for the determination of triglyceride, and in the use of the abovementioned procedure or of the diagnostic product for the in-vitro diagnosis or determination of risk of vascular disorders.

According to the invention, it has surprisingly been found that the use of block copolymers synthesized from polypropylene oxide units and polyethylene oxide units, as a particular type of non-ionic surface-active agents, allows an excellent selectivity of the triglyceride determination with respect to only one or certain classes of lipoprotein fractions. A particularly high selectivity owing to the use of the polyoxypropylene/polyoxyethylene block copolymers (abbreviated POP/POE below) is obtained in relation to the LDL lipoprotein fraction, such that the procedure according to the invention is particularly highly suitable for the selective determination of LDL triglyceride. Such a selectivity for the determination of triglyceride from LDL lipoprotein makes the diagnosis particularly meaningful for the area concerned here.

A particular advantage of the invention consists in the fact that the differentiation according to lipoprotein fractions takes place from homogeneous solution. A specific fractionation step, as was necessary according to the conventional procedure described at the outset, is therefore no longer necessary in the procedure according to the invention. In particular, no precipitation step for the separation of specific lipoprotein fractions is necessary, so that the determination of triglyceride can be carried out without a centrifugation step. As furthermore, owing to the use of the specific non-ionic surface-active agent, turbidity of the homogeneous solution can be avoided, it is possible to determine and to quantify the amount of triglyceride from the selectively solubilized lipoprotein fraction in a simple and rapid manner. This makes the procedure according to the invention particularly readily accessible to routine diagnosis as an easily automatable system.

As a basis for these advantageous actions, it is suspected that the use of POP—POE as a non-ionic surface-active agent makes possible a selective solubilization of specific lipoprotein fractions, so that the triglyceride originally associated with this lipoprotein fraction is made accessible and reactive to the determination and detection reagents for triglyceride, whereas other lipoprotein fractions are solubilized less strongly to not at all and thus the triglyceride contained therein is not accessible to determination and quantification. The selectivity in relation to the individual lipoprotein fractions can be adjusted, as desired, by means of the composition of the POP/POE block copolymer. If it is taken into consideration that a block copolymer of this type is synthesized from a relatively hydrophilic block A having ethylene oxide units and a relatively hydrophobic block B having propylene oxide monomers, by variation of the block units, both within the respective block unit A or B and in the ratio of these units to one another, specific block copolymers can form, which then produce a desired selectivity for the solubilization of a specific lipoprotein or of a group of two lipoprotein classes. Suitable influencing parameters here are the degree of polymerization or the polymerization length within the individual block units A or B and the arrangement and proportioning of the block units relative to the total copolymer. A general overview of block copolymers of propylene oxide and ethylene oxide, from which the materials then suitable for the solubilization of individual lipoprotein fractions can be selected, results from the review articles of I. R. Schmolka in J. Am. Oil Chem. Soc. 54, p. 110 (1977), M. A. Plant in R. D. Karsa (Ed.): "Industrial Applications of Surfactants", The Royal Society of Chemistry, London, p. 318–332 (1986) and K. Kosswig in "Ulmann's Encyclopaedia of Industrial Chemistry", Vol. A 25, p. 747–817, "Surfactants", in particular Chapter 10.1 (1994), where the last-mentioned reference also gives a list of the possible manufacturers.

As the diagnostic meaningfulness as a result of a selective determination of LDL-associated triglyceride is particularly good, in the following the POP/POE block copolymers are described in greater detail which are distinguished by an excellent selectivity for the solubilization of LDL and the making accessible associated therewith of LDL-associated triglyceride to determination and detection reagents.

According to this preferred embodiment of the present invention, the block copolymer consists of a triblock copolymer A—B—A of polyoxyethylene blocks A and a central polyoxypropylene block B. It has emerged that a particularly high selectivity for the determination of LDL triglyceride results when the molecular weight of the POP/POE triblock polymer A—B—A is in the range from 1000 to 8000. The observance of the ratio of the central hydrophobic block constituent B to the terminal hydrophilic block constituents A furthermore has a particularly favourable effect. It was found that the selectivity for the solubilization of LDL triglyceride is particularly favourable if the molecular partial mass of the polyoxypropylene block B with respect to the total triblock copolymer A—B—A is in the range from 75 to 95%, in particular from 85 to 95%. It is assumed that in the case of the observation of the above conditions the hydrophilic/lipophilic balance (HLB) is adjusted such that the structure in the LDL fraction is destabilized, while the structures in the other lipoprotein fractions (HDL, VLDL and CM) remain relatively stable, and thus the triglycerides contained therein are not available or are only available to a relatively small extent for the determination. Consequently, it results from the abovementioned findings that the selectivity in relation to LDL triglyceride is increased with the hydrophobicity accompanying the increase in the molecular mass fraction of the POP block B.

The amount of the POP/POE block copolymer in a reagent formulated for reaction with a triglyceride lipoprotein-containing sample is suitably in the range from 0.001 to 10% by weight, preferably from 0.01 to 5% by weight and in particular from 0.1 to 1% by weight.

Moreover, it has been found that the selectivity in relation to individual lipoprotein fractions can be increased in the context of the procedure according to the invention by reacting the lipoprotein-containing samples further with agents for the aggregation of lipoprotein fractions. The basis for this selectivity increase by aggregating agents is suspected to lie in the fact that the lipoprotein fractions, which are less strongly solubilized by the appropriately selected POP/POE material, are additionally stabilized by the aggregation.

Examples of suitable agents for the aggregation of lipoprotein fractions include heparin or its salt, phosphotungstic acid or its salt, dextransulphuric acid or its salt, polyethylene glycol, sulphatized cyclodextrin or its salt, sulphatized oligosaccharide or its salt, and mixtures thereof. Examples of cyclodextrin include α-cyclodextrin, β-cyclodextrin and γ-cyclodextrin. Examples of the oligosaccharide include maltotriose, maltotetraose, maltopentaose, maltohexaose and maltoheptaose. Salts which can be used are, for example, the sodium, potassium, lithium, ammonium and magnesium salts.

A preferred aggregating agent is cyclodextrin or a cyclodextrin derivative. In particular when using sulphatized α-cyclodextrin, it has advantageously been shown that the selectivity is improved with respect to LDL-associated triglyceride.

A further preferred aggregating agent is dextran-sulphuric acid or its salt dextran sulphate.

Again, with respect to the preferred selectivity according to the invention in relation to LDL triglyceride, it was found that a combination of sulphatized α-cyclodextrin with dextran sulphate in particular had an increased action. For assistance or stabilization of the aggregation of the lipoprotein fractions which are not specifically to be solubilized by the specific POP/POE surface-active agent, in addition to the aggregating agent, salts of divalent metal ions should furthermore be employed. Examples of suitable divalent metal ions are magnesium, manganese, calcium, nickel and cobalt, magnesium being preferred.

The amounts of the aggregating agents, or the salts of divalent metal ions, optionally to be employed can be adapted to the respective case taking into account the desired selectivity with respect to individual lipoprotein fractions and the nature of the aggregating agent. The preferred lower limit content is in this case fixed by a desired and detectable stabilization effect, while the preferred upper limit content is fixed by the avoidance of appearance of turbidity and in particular the avoidance of precipitation, which would prevent a direct triglyceride determination from homogeneous solution.

Suitable amounts of the abovementioned constituents contained in an appropriately formulated reagent lie in the following ranges: 0.02 to 10 mM heparin having a molecular weight of 5000 to 20,000 or its salt, 0.1 to 10 mM phosphotungstic acid having a molecular weight of 4000 to 8000 or its salt, 0.01 to 5 mM dextransulphuric acid having a molecular weight of 10,000 to 500,000 or 0.1 to 20 mM dextransulphuric acid having a molecular weight of 1000 to 10,000 or its salts, 0.3 to 100 mM polyethylene glycol (PEG) having a molecular weight of 4000 to 25,000, 0.1 to 50 mM sulphatized cyclodextrin having a molecular weight of 1000 to 3000 or its salt, 0.1 to 50 mM sulphatized oligosaccharide having a molecular weight of 400 to 3000 or its salt, and mixtures thereof. 0.03 to 1 mM heparin having a molecular weight of 14,000 to 16,000 or its salt, 0.1 to 3 mM phosphotungstic acid having a molecular weight of 5000 to 7000 or its salt, 0.01 to 5 mM dextran sulphate having a molecular weight of 150,000 to 250,000 or its salt, 0.1 to 10 mM dextran sulphuric acid having a molecular weight of 1000 to 5000 or its salt, 1.0 to 50 mM PEG having a molecular weight of 5000 to 22,000, 0.1 to 10 mM sulphatized cyclodextrin having a molecular weight of 1000 to 2000 or its salt, 0.1 to 10 mM sulphatized oligosaccharide having a molecular weight of 400 to 2000 or its salt, and mixtures thereof are preferred.

The concentration of the salt of divalent metal ions is suitably 0.1 to 50 mM, preferably 1 to 5 mM.

The further measure b) of the procedure according to the invention consists in the carrying-out of a triglyceride determination method. For this, determination methods which are known per se and, for example, the determination methods employed in the conventional lipoprotein triglyceride determination procedures mentioned at the outset can be employed. In this case, the use of the enzymatic determination methods customarily carried out has an advantageous effect for the concept according to the invention, since the enzymes employed for this are able, on the one hand, to reach the triglyceride in the specifically destabilized or solubilized lipoprotein fractions and thus to react (which primarily relates to the enzymatic cleavage of triglyceride with formation of glycerol), whereas the lipoprotein fractions not solubilized as a matter of priority and lipoprotein fractions optionally additionally stabilized by aggregating agents protect the triglyceride associated there from the enzymatic reaction.

The enzymatic cleavage is expediently carried out with the aid of lipase or an esterase. The glycerol released thereby can be determined and quantified by enzymatic photometric tests and in particular by means of colour detection reactions. An overview of commercially obtainable tests for carrying out the triglyceride determination is given by A. Bruckner and M. Moret in J. Clin. Chem. Clin. Biochem., Vol. 21, p. 97–106 (1983).

According to the invention, a determination method has proved particularly sensitive which consists in determining the glycerol released as described beforehand by enzymatic reaction using the enzymes glycerokinase and glycerol 3-phosphate dehydrogenase, by means of which a reduced acceptor of reduction/oxidation equivalents, such as NAD or FMN, is formed, which for its part is then determined by a detection reaction.

As a sensitive detection reaction, the carrying-out of a colour reaction is recommended, in which, by means of an electron coupler, a dye is reduced by the reduced acceptor or reduction/oxidation equivalents such as NADH or $FMNH_2$, the reduced form of which dye can be determined photometrically by means of the corresponding absorption wavelength. Suitable electron couplers are, for example, the enzyme diaphorase or the synthetic phenacin methosulphate. Examples of dyes are tetrazolium salts, such as Tetrazolium Blue, Nitro Blue Tetrazolium (NBT), Tetrazolium Violet, Tetrazolium Purple and 2-(p-iodophenyl)-3-(p-nitrophenyl)-5-phenyltetrazolium chloride (INT). These dyes react with formazan formation to give dyes which can be photometrically determined and quantified at the appropriate absorption wavelength, in the case of NBT or INT, for example, at 570 nm.

Other examples, in particular with respect to a high sensitivity, include fluorometric and luminometric determinations.

A further sensitivity increase in connection with the carrying-out of the triglyceride determination method is obtained by including the enzymatic reaction with the released glycerol in addition to the use of the enzymes triosephosphate isomerase and glyceraldehyde 3-phosphate dehydrogenase. The sensitivity increase results in that, per molecule of glycerol released, not only one, but two molecules of reduced reduction/oxidation equivalent are produced. Per glycerol molecule released, two molecules of reduced reduction/oxidation equivalents, such as NADH or FADH, are accordingly available, which consequently also doubles the detection sensitivity.

A particular advantage of the invention results from the fact that both the reaction of triglyceride-containing lipoprotein with the specific POP/POE surface-active agent (measure a)) and the carrying-out of the triglyceride determination method (measure b)) can be allowed to proceed simultaneously.

Owing to this, the two-stage procedure which is conventionally necessary is reduced to a one-stage procedure. Furthermore, labour- and time-consuming fractionation steps are no longer necessary; the incubation according to measure a) and the triglyceride determination according to measure b) can be carried out simultaneously in one batch or at least overlapping in terms of time. If, according to the preferred embodiment of the present invention for increasing the selectivity, an agent for the aggregation of lipoproteins and, if appropriate, furthermore the salt of divalent metal ions is used, however, it has proved expedient first to incubate these constituents with the sample to be determined briefly (for example for a couple of minutes), and only then to add the specific POP/POE surface-active agent and the reagents for the triglyceride determination to this batch. After a further incubation time of a few minutes, the appropriate detection, for example the described photometric determination, can then be carried out.

The incubation for selectively making accessible or releasing triglyceride from specific lipoprotein fractions and the simultaneous or subsequent carrying-out of the triglyceride determination method takes place in a suitable buffer system, which is preferably buffered to a pH range of 5 to 9 and in particular of approximately 6.5 to 9. A glycylglycine buffer or a tris buffer, for example, in a concentration of 5 to 500 mM is suitable. A donor of energy-rich phosphate groups, such as ATP (e.g. 0.1 mM to 50 mM ATP), a calcium ion chelator such as EDTA (e.g. 0 to 5 mM EDTA) and magnesium salt such as $MgCl_2$ (e.g. 1 mM to 50 mM) are moreover suitably employed for the enzymatic reactions.

For the practical implementation of the procedure according to the invention, the triglyceride-associated, lipoprotein-containing biological sample, which as a rule consists of a blood sample (serum or plasma) or of a urine sample, is mixed with the reagent containing the constituents described beforehand at a suitable dilution, which is approximately in the range from 0.1:100 to 10:100 and in particular in the range from 0.5:100 to 2:100. In the case of the preferred use of the aggregating agent and, if appropriate, of the divalent metal ions, a dilution mixture is first prepared in the manner described beforehand using the reagent containing these constituents and briefly incubated, after which the reagent is then added with the agents described for measures a) and b).

The invention furthermore makes available a diagnostic product which is particularly suitable for carrying out the procedure according to the invention, which—in at least one reagent of the diagnostic product—as constituent a) (corresponding to procedure measure a)) includes the specific surface-active agent described beforehand and, as constituent b) (corresponding to procedure measure b)) the described agent(s) for the determination of triglyceride. With respect to the description of constituent a) and of constituent b), reference can be made to the above description of the corresponding procedure measures.

In order that the incubation with the surface-active agent and the incubation for the triglyceride determination proceed simultaneously in an advantageous manner, the diagnostic product is preferably designed as a kit, and the constituents a) and b) are in this case combined in one reagent or two reagents of the diagnostic kit.

In a preferred embodiment of the diagnostic product, this furthermore contains as a further constituent agents for the aggregation of lipoprotein fractions and, if appropriate, a salt of divalent metal ions. Reference can also be made in this respect to the above description. The agent(s) for the aggregation, and, if appropriate, the salt of divalent metal ions is or are preferably contained in a reagent of the diagnostic kit which is different from the reagent comprising the above-mentioned constituents a) and b). This allows the above-described, advantageous preference of the incubation of the sample to be determined with the stabilizing aggregating agents, before the reaction with the specific surface-active agent and the optionally simultaneous carrying-out of the triglyceride determination follows.

The present invention is distinguished by a high selectivity in relation to lipoprotein fractions in homogeneous, liquid phase. This applies in particular to the selective determination of LDL triglyceride under the conditions described above.

On comparison with conventional determination procedures, it was found that the results obtained by means of the invention correlate very well with those of the prior art. However, according to the invention a small amount of the sample to be investigated suffices, and the specific lipoprotein-associated triglyceride can be determined in a short time of even a few minutes. The determination can furthermore be carried out directly from the homogeneous phase, so that two-stage processes which include complicated fractionation steps are no longer necessary.

The present invention is therefore excellently suited for simple and reliable routine diagnosis and ought to be accessible to automation. A diagnostic possibility which suggests itself is primarily the use of the procedure or diagnostic product according to the invention for the in-vitro diagnosis or determination of the risk of vascular diseases.

In this connection, the determination of LDL triglycerides as a universal risk indicator for coronary heart disease, furthermore for diabetic macro- and microangiopathy and as an indicator for LDL of atypical composition (type III hyperlipoproteinaemia according to Fredrickson) can be mentioned in particular.

The invention is illustrated in greater detail below by means of the following examples.

EXAMPLE 1

For the selective determination of LDL triglyceride, a reagent having the following constituents was first formulated.

POP/POE triblock copolymer, molecular weight 4500, POP/POE proportion 90% by weight: 0.1% by weight
Lipase: 10 kU/l
Glycerokinase: 4.8 kU/l
Glycerol 3-phosphate dehydrogenase: 48 kU/l
Triosephosphate isomerase: 300 kU/l
Glyceraldehyde 3-phosphate dehydrogenase: 24 kU/l
Diaphorase: 4.8 kU/l
ATP: 5 mM
NAD: 5 mM
EDTA: 0.5 mM
4-NBT: 3 mM
Glycylglycine buffer (pH 7.5): 0.2 M, made up to 100% by weight.

4 µl of a serum sample were added to 400 µl of this reagent and incubated at 37° C. for 5 min. The dye formed up to this time was determined photometrically at 570 nm.

For quantification, a standardization measurement was additionally carried out. For this, a defined amount of LDL triglyceride isolated by ultracentrifugation was initially added (5 g/l) and diluted to a dilution of 1:10 with isotonic saline solution (0.9% by weight) in a fixed dilution series. The respective dilutions were measured analogously to the procedure described beforehand. A linear standard curve resulted within the prepared dilution series.

Furthermore, for the specific quantification of LDL triglyceride from the serum sample, the total triglyceride was determined using a commercially obtainable serum triglyceride test.

In a comparison with conventional, two-stage determination procedures such as ultracentrifugation and the precipitation technique, adequately corresponding values resulted by means of the procedure according to the invention.

EXAMPLE 2

Example 1 was repeated in the same manner with the assumption that, instead of the POP/POE block copolymer employed there, one having a molecular partial mass of the POP block with respect to the total block copolymer of 70% by weight was used.

The result obtained showed that the reactivity of the triglyceride determination with respect to the specific LDL species was admittedly just as good as in Example 1, but that an—even if slight—reactivity to other lipoprotein species was to be observed. Consequently, although the selectivity with respect to the LDL triglyceride determination was still practically acceptable, it was somewhat poorer than in Example 1.

EXAMPLE 3

A first reagent having the following constituents was initially formulated:
Sulphatized α-cyclodextrin: 0.5 mM
Dextran sulphate (molecular weight 200,000): 1 mM
$MgCl_2$: 2.5 mM
Glycylglycine buffer (pH 7.2): 0.2 M, made up to 100% by weight.

For carrying out the specific LDL triglyceride determination, 4 μl of the serum sample were added to 300 μl of this reagent, and the mixture was incubated at 37° C. for 5 min. 100 μl of a reagent analogous to Example 1, in which the concentration of the reagent constituents apart from those of the buffer was four time higher, were added and the mixture was again incubated for 5 min. The measurement of the LDL triglyceride, the comparison with the standard curve and the total serum triglyceride measurement were carried out in the same manner as described in Example 1.

The results obtained showed an even better agreement with the conventional, two-stage triglyceride determination procedures and thus an even better selectivity of the LDL triglyceride determination.

What is claimed is:

1. Procedure for the determination of triglyceride contained in low density lipoprotein (LDL) having the following measures:
   a) selective solubilization of triglyceride-containing low density lipoprotein with a non-ionic surface-active agent, which is synthesized from a block copolymer of propylene oxide and ethylene oxide, and
   b) carrying-out of a triglyceride determination method.

2. Procedure according to claim 1, characterized in that it is carried out in homogeneous solution.

3. Procedure according to claim 1, characterized in that the block copolymer used is an A—B—A triblock copolymer of polyoxyethylene blocks A and central polyoxypropylene block B.

4. Procedure according to claim 3, characterized in that the molecular weight of the polyoxypropylene/polyoxyethylene triblock copolymer A—B—A is in the range from 1000 to 8000 Daltons.

5. Procedure according to claim 4, characterized in that the molecular partial mass of the polyoxypropylene block B with respect to the total triblock copolymer A—B—A is in the range from 75 to 95% by weight.

6. Procedure according to claim 1, characterized in that the selective solubilization according to measure a) and the triglyceride determination according to measure b) are carried out simultaneously.

7. Procedure according to claim 1, characterized in that the triglyceride-containing in low density lipoproteins are furthermore reacted with agents for the aggregation of lipoprotein fractions.

8. Procedure according to claim 7, characterized in that the agent used for the aggregation of lipoprotein fractions is cyclodextrin or cyclodextrin derivative.

9. Procedure according to claim 8, characterized in that sulphatized α-cyclodextrin is used.

10. Procedure according to claim 7, characterized in that dextransulphuric acid or its salt is used as an agent for the aggregation of lipoprotein fractions.

11. Procedure according to claim 7, characterized in that the reaction with the aggregating agent is carried out in the presence of divalent metal ions.

12. Procedure according to claim 7, characterized in that the reaction with the aggregating agent is carried out before measures a) and b).

13. Procedure according to claim 1, characterized in that the determination of triglyceride according to measure b) includes the enzymatic cleavage of triglyceride and the determination of the glycerol released thereby.

14. Procedure according to claim 13, characterized in that the enzymatic cleavage is carried out with the aid of lipase or an esterase.

15. Procedure according to claim 13, characterized in that the released glycerol is determined by enzymatic reaction with the enzymes glycerokinase and glycerol 3-phosphate dehydrogenase, by means of which a reduced acceptor of reduction/oxidation equivalents is formed, which is determined by a detection reaction.

16. Procedure according to claim 15, characterized in that the enzymes triosephosphate isomerase and glyceraldehyde 3-phosphate dehydrogenase are furthermore added to the enzymatic reaction.

17. Procedure according to claim 1, wherein the results of the procedure are indicative of risk of vascular disease.

* * * * *